(12) United States Patent
Jensen et al.

(10) Patent No.: US 11,717,182 B2
(45) Date of Patent: Aug. 8, 2023

(54) ABDOMINAL MEASUREMENT APPARATUSES AND RELATED METHODS

(71) Applicant: Mayo Foundation for Medical Education and Research, Rochester, MN (US)

(72) Inventors: Michael D. Jensen, Rochester, MN (US); Teresa B. Jensen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 670 days.

(21) Appl. No.: 16/641,381

(22) PCT Filed: Aug. 21, 2018

(86) PCT No.: PCT/US2018/047306
§ 371 (c)(1),
(2) Date: Feb. 24, 2020

(87) PCT Pub. No.: WO2019/040480
PCT Pub. Date: Feb. 28, 2019

(65) Prior Publication Data
US 2021/0393165 A1  Dec. 23, 2021

Related U.S. Application Data (60) Provisional application No. 62/550,214, filed on Aug. 25, 2017.

(51) Int. Cl.
*A61B 5/107* (2006.01)
*A61B 5/00* (2006.01)
*A41H 1/02* (2006.01)

(52) U.S. Cl.
CPC .............. *A61B 5/1073* (2013.01); *A41H 1/02* (2013.01); *A61B 5/002* (2013.01); *A61B 5/1072* (2013.01);
(Continued)

(58) Field of Classification Search
CPC ................................ A61B 5/1073; A41H 1/02
(Continued)

(56) References Cited

U.S. PATENT DOCUMENTS

| 3,327,394 A | 6/1967 | Tenteris |
| 4,185,390 A | 1/1980 | Tateishi |

(Continued)

FOREIGN PATENT DOCUMENTS

| CN | 103416884 | 12/2013 |
| EP | 1222438 | 4/2007 |

(Continued)

OTHER PUBLICATIONS

Bellisari, "Sonographic measurement of adipose tissue," Journal of Diagnostic Medical Sonography, 1993, 9(1):11-18.
(Continued)

*Primary Examiner* — Amir Shahnami
(74) *Attorney, Agent, or Firm* — Fish & Richardson P.C.

(57) ABSTRACT

An abdominal measurement apparatus includes multiple belts configured to be lengthened and shortened around respective portions of an abdomen, multiple tensioning mechanisms respectively coupled to the multiple belts and configured to maintain substantially constant tensions in the multiple belts around the respective portions of the abdomen, and multiple measurement devices respectively coupled to the multiple belts and configured to provide indications of lengths of the multiple belts while the multiple belts are maintained in tension around the respective portions of the abdomen.

15 Claims, 9 Drawing Sheets

(52) U.S. Cl.
CPC .......... *A61B 5/6802* (2013.01); *A61B 5/6823* (2013.01); *A61B 5/6831* (2013.01)

(58) Field of Classification Search
USPC .......................................................... 33/512
See application file for complete search history.

(56) References Cited

U.S. PATENT DOCUMENTS

| | | | |
|---|---|---|---|
| 4,308,872 | A | 1/1982 | Watson et al. |
| 4,473,949 | A | 10/1984 | Schechtman |
| 5,178,151 | A | 1/1993 | Sackner |
| 6,817,110 | B2 | 11/2004 | Bohnengel |
| 7,599,537 | B1 | 10/2009 | Stefan et al. |
| 7,678,063 | B2 | 3/2010 | Felmlee et al. |
| 8,161,826 | B1 | 4/2012 | Taylor |
| 8,374,671 | B2 | 2/2013 | Barnes |
| 9,078,586 | B2 | 7/2015 | Fukuda et al. |
| 9,167,857 | B2 | 10/2015 | Jang et al. |
| 2001/0030754 | A1 | 10/2001 | Spina et al. |
| 2006/0213944 | A1* | 9/2006 | Dieter ...................... A45F 3/04 224/648 |
| 2011/0295144 | A1 | 12/2011 | Murakawa et al. |
| 2014/0275829 | A1* | 9/2014 | Berezhnyy ........... A61B 5/6892 600/372 |
| 2016/0153853 | A1 | 6/2016 | Brenner et al. |
| 2016/0165988 | A1* | 6/2016 | Glasgow ............ G06Q 30/0269 703/11 |
| 2016/0302724 | A1 | 10/2016 | Coulm et al. |
| 2018/0070865 | A1* | 3/2018 | Balko .................. A61B 5/4806 |

FOREIGN PATENT DOCUMENTS

| | | |
|---|---|---|
| EP | 2581701 | 4/2013 |
| GB | 160441 | 7/1921 |
| TW | 201350036 | 12/2013 |
| WO | WO 2004011873 | 2/2004 |
| WO | WO 2012082034 | 6/2012 |

OTHER PUBLICATIONS

BodyVolume.com [online], "What is BVI?," dated Mar. 22, 2017, available on or before Oct. 15, 2010, via Internet Archive: Wayback Machine URL<https://web.archive.org/web/20101015230537/http://www.bodyvolume.com/what_is_bvi>, retrieved on Dec. 15, 2020, retrieved from URL<https://web.archive.org/web/20170322212719/http://www.bodyvolume.com/what_is_bvi>, 2 pages.

Jang et al., "A basic study for automatic waist circumference measurement using magnet with waist belt to assist obese management in daily life," 30th Annual International Conference of the IEEE EMBS, Vancouver, CA, Aug. 20-24, 2008, 2008:2333-2336.

Jang et al., "Development of an integrated obesity management waist belt system composed of calorie tracking and waist circumference measuring module for long term monitoring," 33rd Annual International Conference of the IEEE EMBS, Boston, MA, Aug. 30-Sep. 3, 2011, 2011:2172-2175.

Lear et al., "The relationship between waist circumference and metabolic risk factors: cohorts of European and Chinese descent," Metabolism, 2002, 51(11):1427-1432.

PCT International Preliminary Report on Patentability in International Appln. No. PCT/US2018/047306, dated Feb. 25, 2020, 7 pages.

PCT International Search Report and Written Opinion in International Appln. No. PCT/US2018/047306, dated Oct. 9, 2018, 8 pages.

Weinberg et al., "Measuring human ventilation for apnoea detection using an optical encoder," Physiological Measurement, 1998, 19(3):441-446.

* cited by examiner

```
COM3 - puTTY
158540: RELAX (in) : 32.47, 31.84, 32.85, 33.44, 33.98
159579: RELAX (in) : 32.47, 31.84, 32.85, 33.44, 33.98
160618: RELAX (in) : 32.47, 31.84, 32.85, 33.44, 33.98
161658: RELAX (in) : 32.47, 31.84, 32.85, 33.46, 34.00
162697: RELAX (in) : 32.48, 31.86, 32.87, 33.49, 34.06
163748: MEASE (in) : 32.48, 31.86, 32.87, 33.49, 34.03
164799: MEASE (in) : 32.48, 31.86, 32.87, 33.49, 34.02
165850: MEASE (in) : 32.48, 31.86, 32.88, 33.49, 34.00
166901: MEASE (in) : 32.48, 31.87, 32.88, 33.49, 34.00
167952: MEASE (in) : 32.48, 31.87, 32.88, 33.49, 33.98
169003: MEASE (in) : 32.48, 31.87, 32.88, 33.47, 33.98
170054: MEASE (in) : 32.48, 31.87, 32.88, 33.47, 33.98
171105: MEASE (in) : 32.48, 31.87, 32.88, 33.47, 33.98
172156: MEASE (in) : 32.48, 31.87, 32.88, 33.47, 33.98
173207: MEASE (in) : 32.48, 31.87, 32.88, 33.47, 33.98
174258: MEASE (in) : 32.48, 31.87, 32.88, 33.47, 33.98
175299: RELAX (in) : 32.48, 31.87, 32.88, 33.47, 33.98
176340: RELAX (in) : 32.48, 31.87, 32.88, 33.47, 33.98
177379: RELAX (in) : 32.48, 31.87, 32.88, 33.47, 33.98
178418: RELAX (in) : 32.48, 31.87, 32.88, 33.47, 33.98
179457: RELAX (in) : 32.48, 31.87, 32.88, 33.47, 33.98
180496: RELAX (in) : 32.48, 31.87, 32.88, 33.47, 33.98
181535: RELAX (in) : 32.48, 31.87, 32.88, 33.47, 33.98
```

ABDOMINAL MEASUREMENT APPARATUSES AND RELATED METHODS

CROSS-REFERENCE TO RELATED APPLICATIONS

This application is a National Stage application under 35 U.S.C. § 371 of International Application No. PCT/US2018/047306, having an international filing date of Aug. 21, 2018, which claims priority to U.S. Provisional Patent Application No. 62/550,214, filed on Aug. 25, 2017, the entire contents of which are incorporated herein by reference.

TECHNICAL FIELD

This disclosure relates to abdominal measurement apparatuses, and more particularly to automated abdominal measurement apparatuses that can determine an abdominal volume.

BACKGROUND

Waist circumference measurement has been established as a better predictor of disease risk (e.g., diabetes risk, obesity risk, etc.) than body mass index (BMI). However, a number of challenges limit the use, accuracy, and reliability of waist circumference measurements. These include improper technique due to inadequate training (resulting in incorrect values), patient unease at having someone measure the patient's waist during a health care visit, and the additional office time associated with acquiring such measurements, as is recommended by national guidelines. Thus, user error and the manual nature of measuring waist circumference account for significant drawbacks to using abdominal measurements to predict disease risk in the medical office or other settings. Given that internal volumes of organs (e.g., liver, kidneys, spleen, intestines, etc.) is similar across patients, whereas abdominal fat can vary widely across patients, abdominal volume may turn out to be an even better predictor of disease risk than an accurately measured waist circumference.

SUMMARY

The present disclosure provides an automated, portable, and lightweight abdominal measurement apparatus that includes a small backpack, a measurement assembly, and a user interface terminal. The abdominal measurement apparatus provides an accurate, reliable measurement of abdominal circumference and/or volume that removes the variability associated with conventional manual measuring tapes used to measure waist circumference. Owing to the small footprint and light weight of the abdominal measurement apparatus, the abdominal measurement apparatus may be transported easily and made readily available in a variety of settings, such as at a home, an office, a medical facility, or a fitness center.

In one aspect, an abdominal measurement apparatus includes multiple belts configured to be lengthened and shortened around respective portions of an abdomen, multiple tensioning mechanisms respectively coupled to the multiple belts and configured to maintain substantially constant tensions in the multiple belts around the respective portions of the abdomen, and multiple measurement devices respectively coupled to the multiple belts and configured to provide indications of lengths of the multiple belts while the multiple belts are maintained in tension around the respective portions of the abdomen.

Embodiments may include one or more of the following features.

In some embodiments, each belt of the multiple belts includes two portions.

In certain embodiments, each tensioning mechanism of the multiple tensioning mechanisms includes two spring-loaded rollers.

In some embodiments, the abdominal measurement apparatus further includes a backpack to which the multiple belts are mounted, the backpack being adjustable to accommodate various sizes of subject torsos.

In certain embodiments, each measurement device of the multiple measurement devices is configured to acquire measurements at a predetermined frequency.

In some embodiments, the abdominal measurement apparatus further includes a processor in communication with the multiple measurement devices.

In certain embodiments, the processor is configured to receive measurements from the multiple measurement devices and to output the measurements to a computing device.

In some embodiments, the processor is configured to wirelessly communicate with the computing device.

In certain embodiments, the abdominal measurement apparatus further includes a user interface terminal by which the abdominal measurement apparatus can be controlled.

In another aspect, a method of measuring an abdomen includes receiving, by a processor, multiple signals that respectively indicate peripheral measurements of an abdomen and determining, by the processor, an index associated with the abdomen based on the multiple signals indicating peripheral measurements of the abdomen. The multiple signals are generated by an abdominal measurement apparatus in contact with the abdomen. The abdominal measurement apparatus includes multiple belts configured to be lengthened and shortened around respective portions of an abdomen, multiple tensioning mechanisms respectively coupled to the multiple belts and configured to maintain substantially constant tensions in the multiple belts around the respective portions of the abdomen, and multiple measurement devices respectively coupled to the multiple belts and configured to provide indications of lengths of the multiple belts while the multiple belts are maintained in tension around the respective portions of the abdomen.

In some embodiments, each belt of the multiple belts includes two portions.

In certain embodiments, the method further includes adjusting a length of one or more of the multiple belts.

In some embodiments, each tensioning mechanism of the multiple tensioning mechanisms includes two spring-loaded rollers.

In certain embodiments, the method further includes receiving, by the processor, the multiple signals at a predetermined frequency.

In some embodiments, the index is an abdominal volume.

In certain embodiments, the index is an abdominal circumference.

DESCRIPTION OF DRAWINGS

Like reference symbols in the various figures indicate like elements. In some examples, illustrations shown in the drawings may not be drawn to scale.

DETAILED DESCRIPTION

Figure 1:
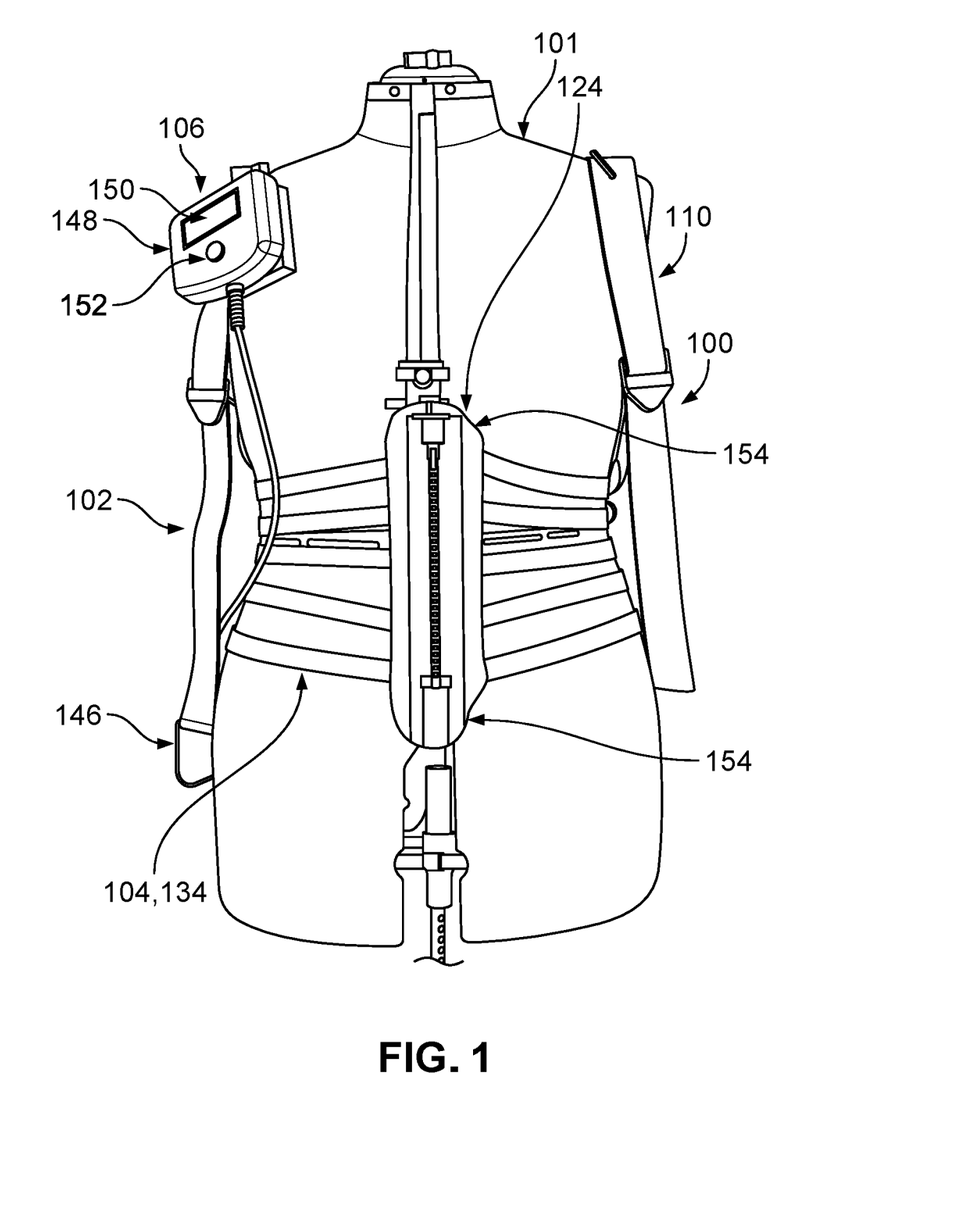
FIG. 1 is a front view of an abdominal measurement apparatus.
Figure 2:
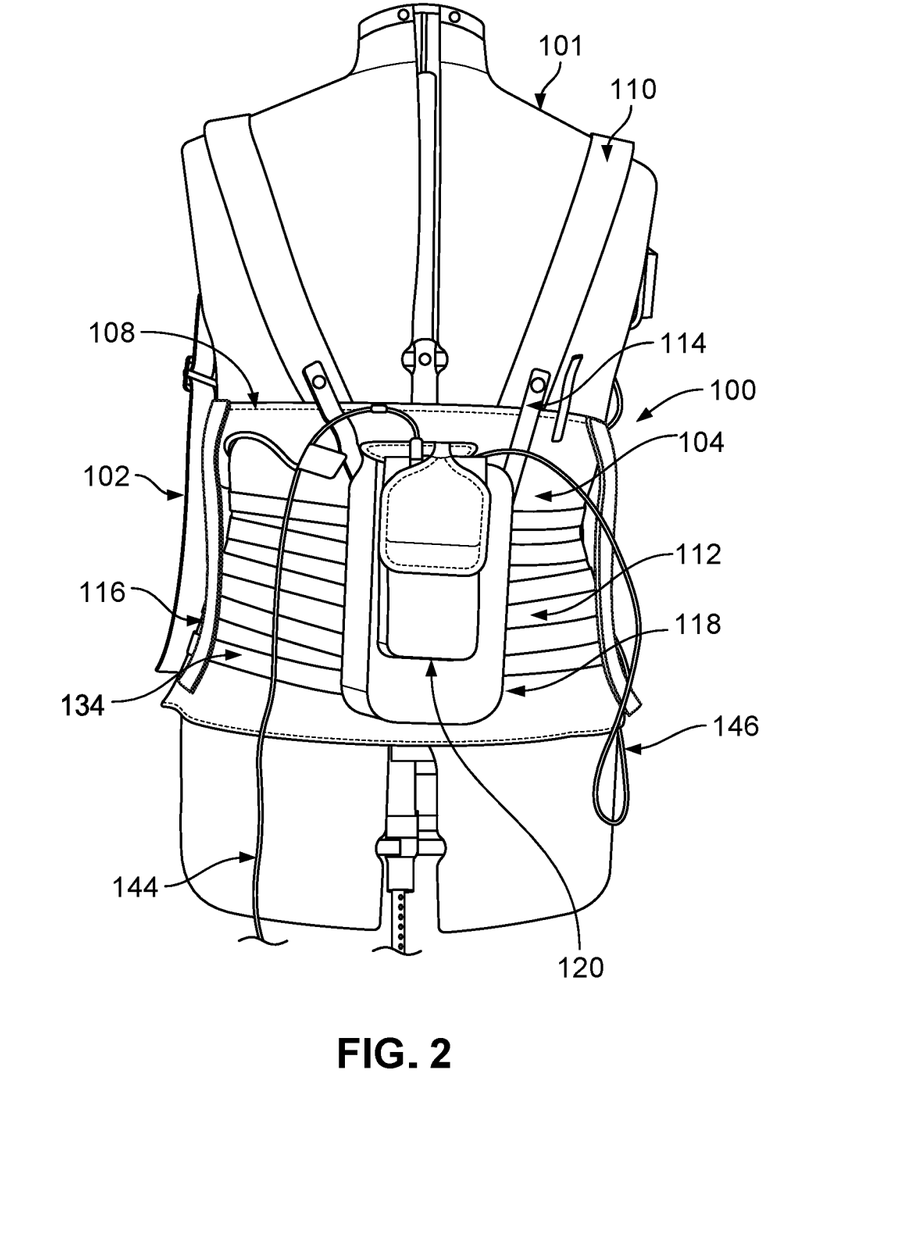
FIG. 2 is a rear view of the abdominal measurement apparatus of FIG. 1.
Figure 3:
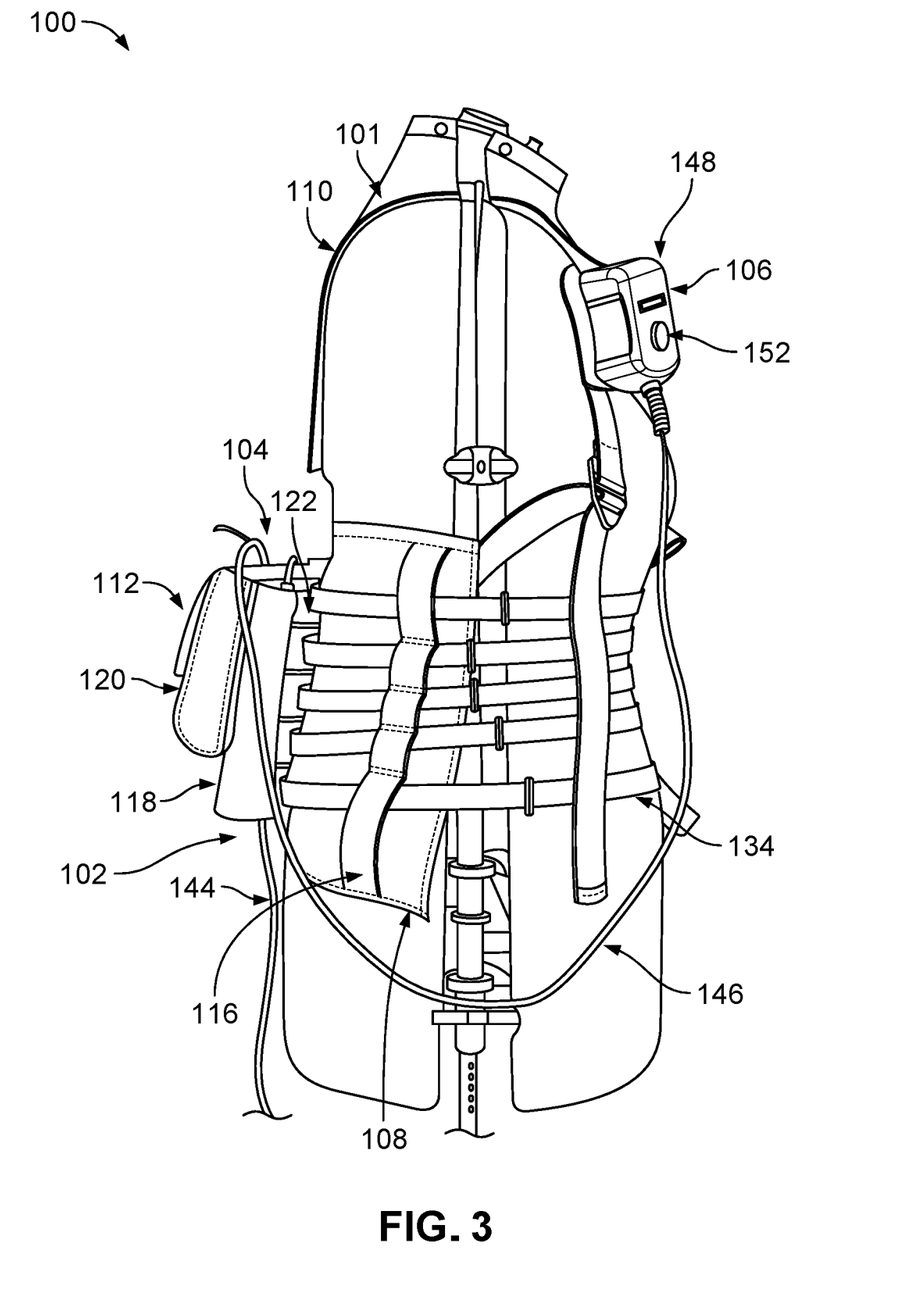
FIG. 3 is a side view of the abdominal measurement apparatus of FIG. 1.

FIGS. 1-3 are front, rear, and side images, respectively, of an abdominal measurement apparatus 100 that determines an abdominal volume of a subject 101. The abdominal measurement apparatus 100 includes a backpack 102, a measurement assembly 104, and a user interface terminal 106. The abdominal measurement apparatus 100 is portable and has a light weight of about 3 lbs to about 4 lbs.

The backpack 102 is typically made of fabric (e.g., nylon or another material) and includes a support band 108, two shoulder straps 110, a centrally located pouch 112 that houses electronics, two anchoring straps 114 that secure a position of the pouch 112, and two guide straps 116 that locate components of the measurement assembly 104, as will be discussed in more detail below. The support band 108 is sized to span an abdomen of the subject 101 and typically has a length of about 48 cm to about 52 cm and a width of about 13 cm to about 15 cm. The length and width of the support band 108 may vary and may be selected in dependence on a size of the subject 101. The shoulder straps 110 are adjustable to accommodate various torso sizes. The pouch 112 includes inner portion 118 and an outer portion 120. The inner portion 118 has a height of about 18 cm to about 22 cm, a width of about 9 cm to about 11 cm, and a depth of about 5 cm to about 6 cm. The outer portion 120 has a height of about 14 cm to about 15 cm, a width of about 7 cm to about 9 cm, and a depth of about 4 cm to about 5 cm. The guide straps 116 are attached to the support band 108 at upper ends, lower ends, and multiple (e.g., four) intermediate points to define multiple (e.g., five) spaces that locate components of the measurement assembly 104.

FIGS. 4-7 are various illustrations of portions of the measurement assembly 104. Referring to FIGS. 1-7, the measurement assembly 104 includes multiple (e.g., five) measurement devices 122, a zipper 124 attached to the measurement devices 122, two clips 154 located at opposing ends of the zipper 124, and a processing module 126 that processes data from the measurement devices 122. Referring particularly to FIGS. 4-7, each measurement device 122 includes two rollers 128 (e.g., spring-loaded rollers) that rotate about respective magnetic encoders 132, two belts 134 that are respectively attached to the rollers 128, a circuit board 136 providing electronics, two encoder readers 138 attached to the circuit board 136 that respectively determine a number of revolutions taken by the rollers 128 and a direction of the revolutions, a cable 140 extending from the circuit board 136 to the processing module 126, and a multi-part enclosure 142 that surrounds the various components of the measurement device 122. The enclosures 142 of the measurement devices 122 are covered by the inner portion 118 of the pouch 112.

The two belts 134 of each measurement device 122 together form a measuring tape that can be lengthened and shortened to accommodate a size the subject 101 according to rotation of the respective rollers 128. The belts 134 are typically made of fabric (e.g., nylon or another material) and extend from the enclosure 142 to the zipper 124 through the spaces formed by the guide straps 116. The fabric from which the belts 134 are made is flexible, but not subject to stretching or shortening such that the belts 134 do not change in length with use. In this manner, the spaces formed by the guide straps 116 serve to maintain a vertical position of the belts 134 around the support band 108 and between the enclosure 142 and the zipper 124. Each belt 134 (i.e., forming half of a measurement tape) has a total extended length of about 35 cm to about 70 cm and a width of about 1 cm to about 3 cm. The belts 134 are typically spaced vertically from each other (e.g., as measured from centerlines of the belts 134) by about 2 cm to about 4 cm (e.g., about 2 cm) over a total height of about 25 cm to about 30 cm.

Figure 4:
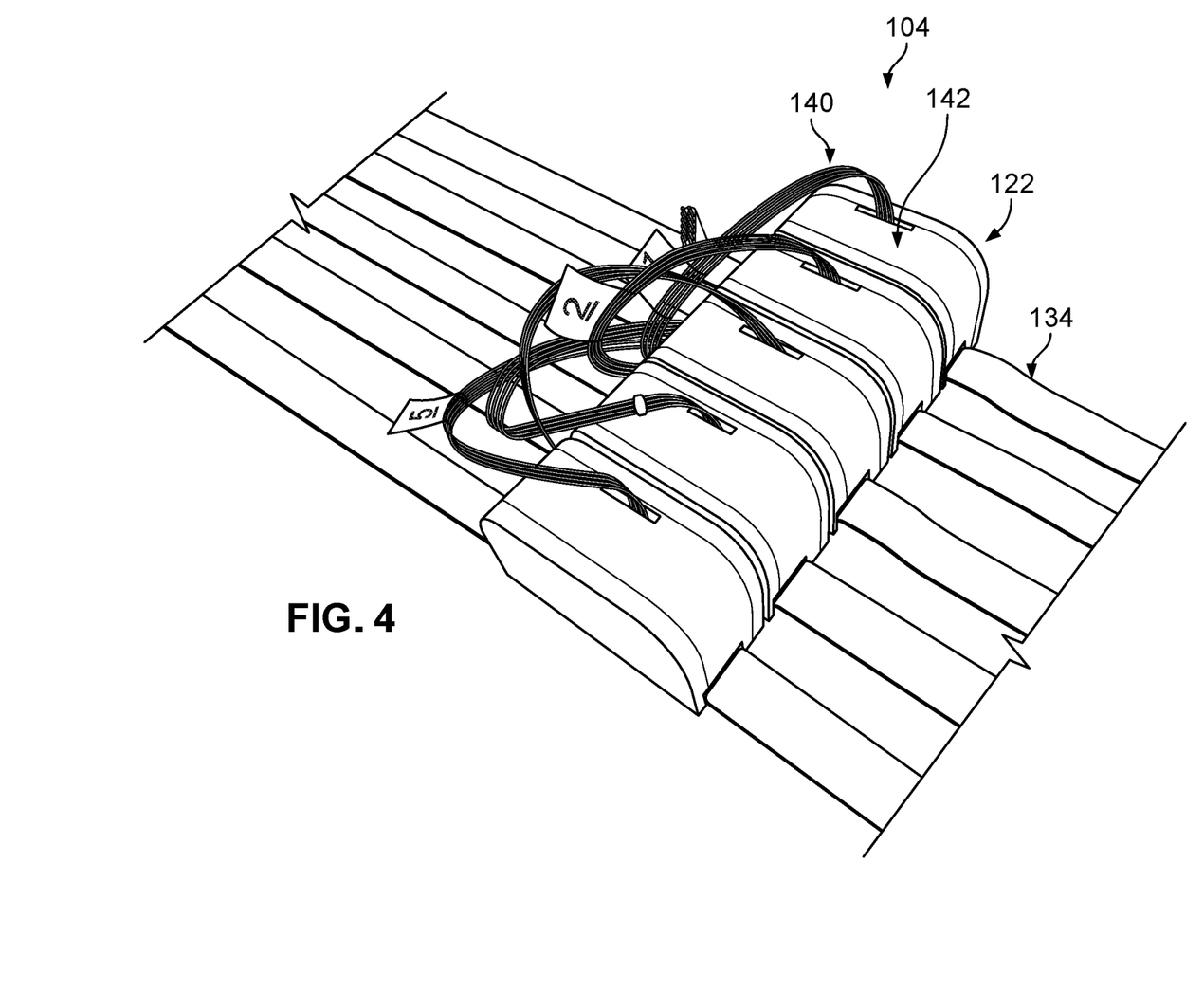
FIG. 4 is a perspective view of a portion of multiple measurement devices of the abdominal measurement apparatus of FIG. 1.
Figure 5:
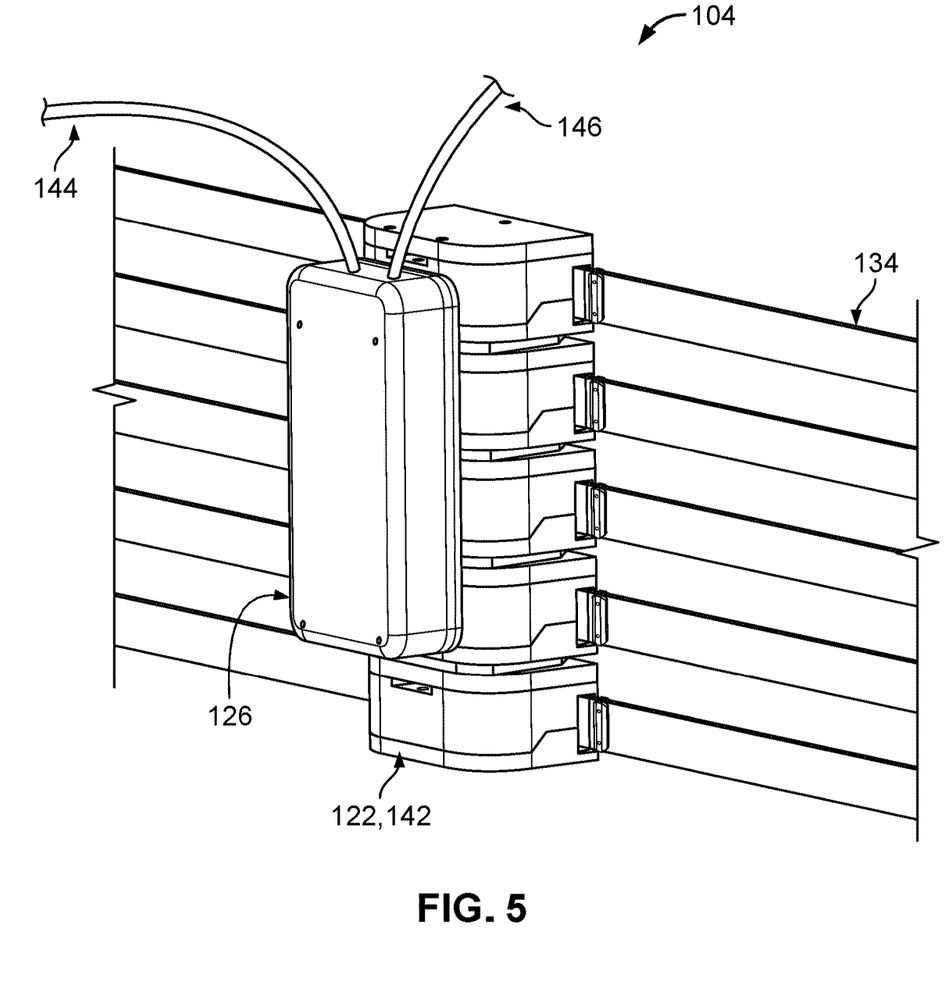
FIG. 5 is a perspective view of a portion of a measurement assembly including the multiple measurement devices of FIG. 4.
Figure 6:
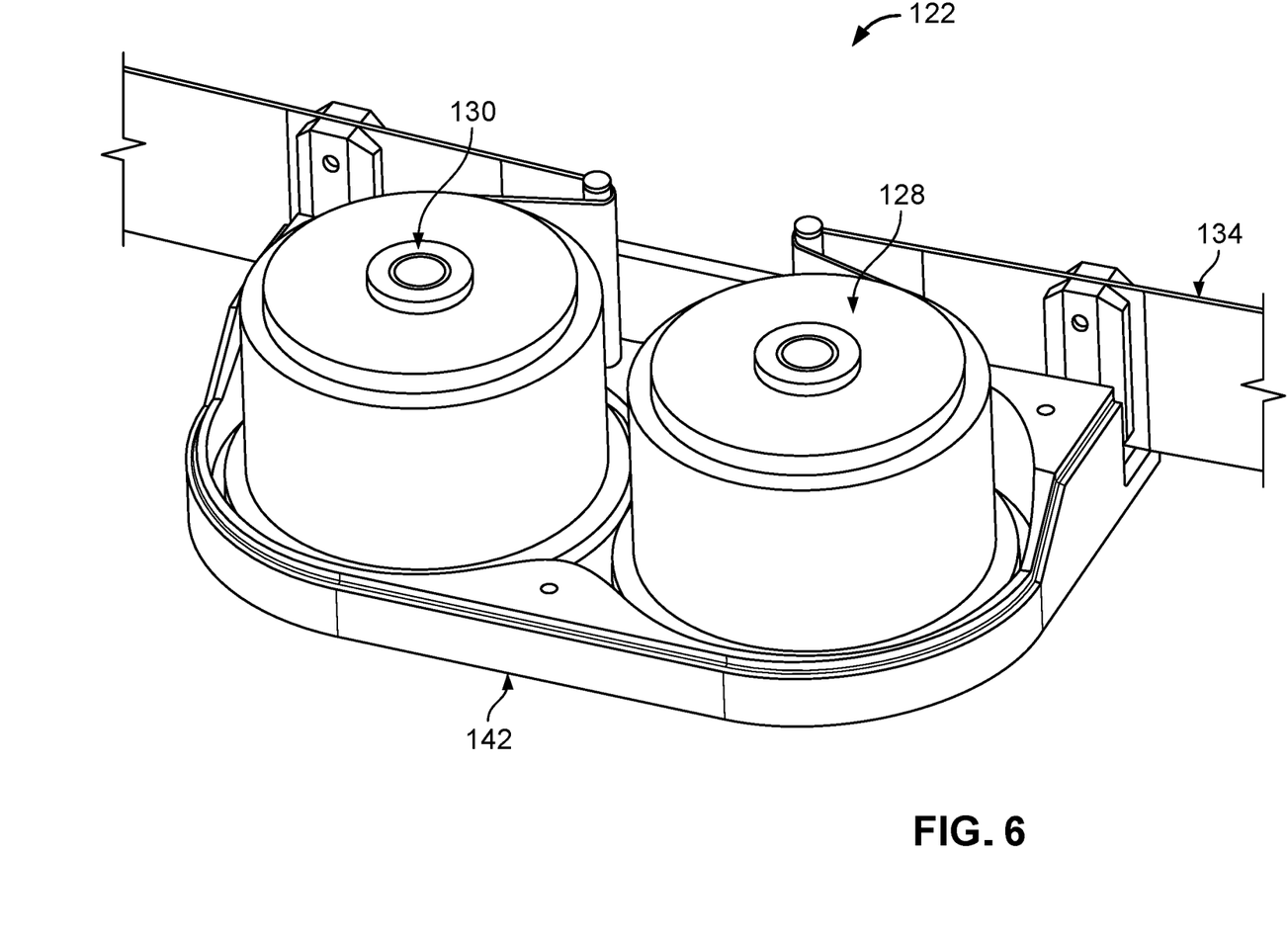
FIG. 6 is a perspective view of an internal portion of one of the multiple measurement devices of FIG. 4.
Figure 7:
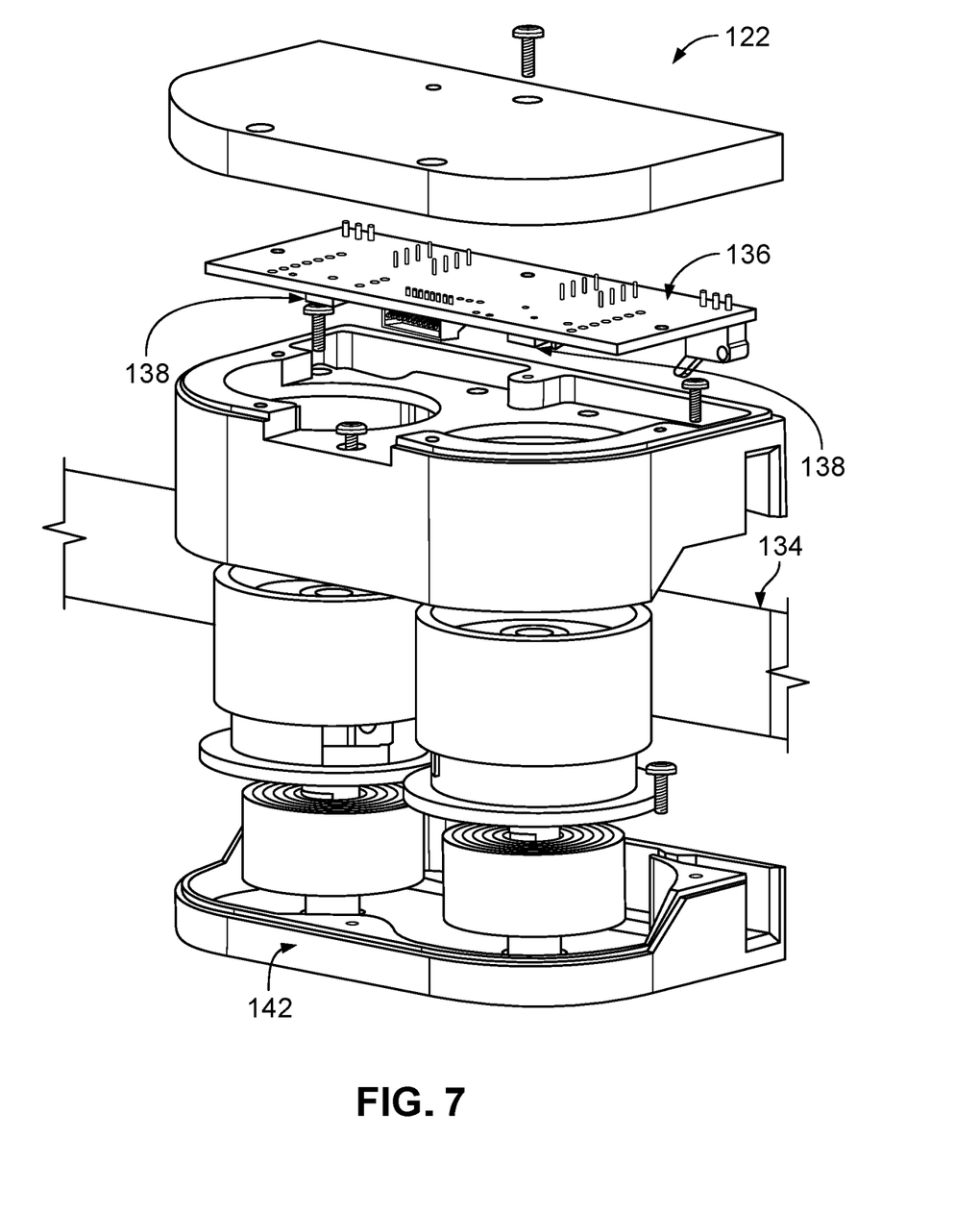
FIG. 7 is an exploded perspective view of a portion of one of the multiple measurement devices of FIG. 4.

The processing module 126 is secured to the measurement devices 122 and houses processing electronics (not shown) to which the cables 140 of the measurements devices 122 are connected. A cable 144 extends from the processing electronics to a computer (not shown), and a cable 146 extends from the processing electronics to the user interface terminal 106. The processing module 126 is covered by the outer portion 120 of the pouch 112.

The user interface terminal 106 is releasably securable to the shoulder straps 110 via a snap button. The user interface terminal 106 includes an enclosure 148, a viewing window 150 on which messages are displayed, and a control button 152 for operating the abdominal measurement apparatus 100.

In operation, a user positions the abdominal measurement apparatus 100 in an open, flat configuration on a generally flat surface. In some implementations, the abdominal measurement apparatus 100 may hang on a wall or be otherwise stored in a position that makes it easy for the user to slip on the abdominal measurement apparatus. The user connects the cable 144 of the processing module 126 to a computer and then opens an application of the processing module 126 to establish communication between the computer and the user interface terminal 106. In some implementations, the cable 144 may already be connected to the computer such that the user interface terminal 106 is ready for use. In some alternative embodiments, the user interface terminal 106 may have an independent power supply and be connected to the computer via a Bluetooth connection. The application starts up the processing module 126, and the measurement devices 122 determine initial, home positions of the rollers 128 and the associated belts 134. The subject 101 puts the abdominal measurement apparatus 100 on by sliding his or her arms through the shoulder straps 108 and then closing the backpack 102 against his or her abdomen by clasping the clips 144 together. Next, the subject 101 adjusts the shoulder straps 110 to snuggly position the shoulder straps 110 in contact with the torso of the subject 101.

The subject 101 then adjusts his or her clothes to ensure that the clothes are generally flat (e.g., smooth and un-bunched) underneath the backpack 102. In order to obtain accurate readings, it will be suggested that the subject 101 wears a single layer of light clothes. The subject 101 also adjusts the belts 134 to ensure that the belts 134 are flat against the abdomen along an entire frontal surface of the abdomen and positions the zipper 124 horizontally at an approximate centerline of the abdomen and vertically approximately at a waistline of the subject 101. The subject 101 zips up the zipper 124, and as the zipper 124 is being zipped, the rollers 128 of the measurement devices 122 adjust (e.g., rotate to lengthen or shorten the belts 134) to produce a constant tension of about 4 pounds to about 7 pounds in the belts 134 such that the belts 134 snuggly contact the abdomen without squeezing the abdomen.

The subject 101 grasps the user interface terminal 106 and presses the control button 152 to activate the processing module 126. The viewing window 150 indicates a type of round occurring (e.g., a measurement round or a relaxation round), an amount of time (in seconds) remaining in the round, and a count of the total number of rounds. The normal breathing motion of the subject 101 often causes the abdomen to expand and contract throughout the round.

During measurement rounds, the belts 134 are lengthened (e.g., unwound) around the abdomen or shortened (e.g., wound) within the respective measurement device 122 by rotation of the spring-loaded rollers 128 such that the constant tension is maintained in the belts 134 as the abdomen expands and contracts. Both belts 134 in a same measurement device 122 are adjusted by an equal amount in opposite roller directions such that both belts 134 are simultaneously lengthened by the same amount or such that both belts 134 are simultaneously shortened by the same amount. The encoder readers 138 of the measurement devices 122 can register 128 counts to 512 counts (e.g., 256 counts) per revolution of the respective rollers 128 and directions of revolutions to determine a length of the belts 134 extended from a respective measurement device 122.

The processing module 126 determines an abdominal circumference associated with the length measurements of the two belts 134 acquired for each measurement device 122. A value of the abdominal circumference may have an error of about 0.08 cm to about 1.00 cm. Each measurement round lasts about 60 seconds and is divided into four, 15 second intervals that are displayed on the user terminal viewing 150 as alternating indications of "measuring" and "relax". The data generated includes about 60 abdominal circumference values (one per second) for each set of belts 134. The tension in the belts 134 remains constant throughout each 60 second measurement round. The indications of "measuring" and "relax" are intended to discourage the subject 101 from holding in his or her abdomen during the measurements.

Figure 8:
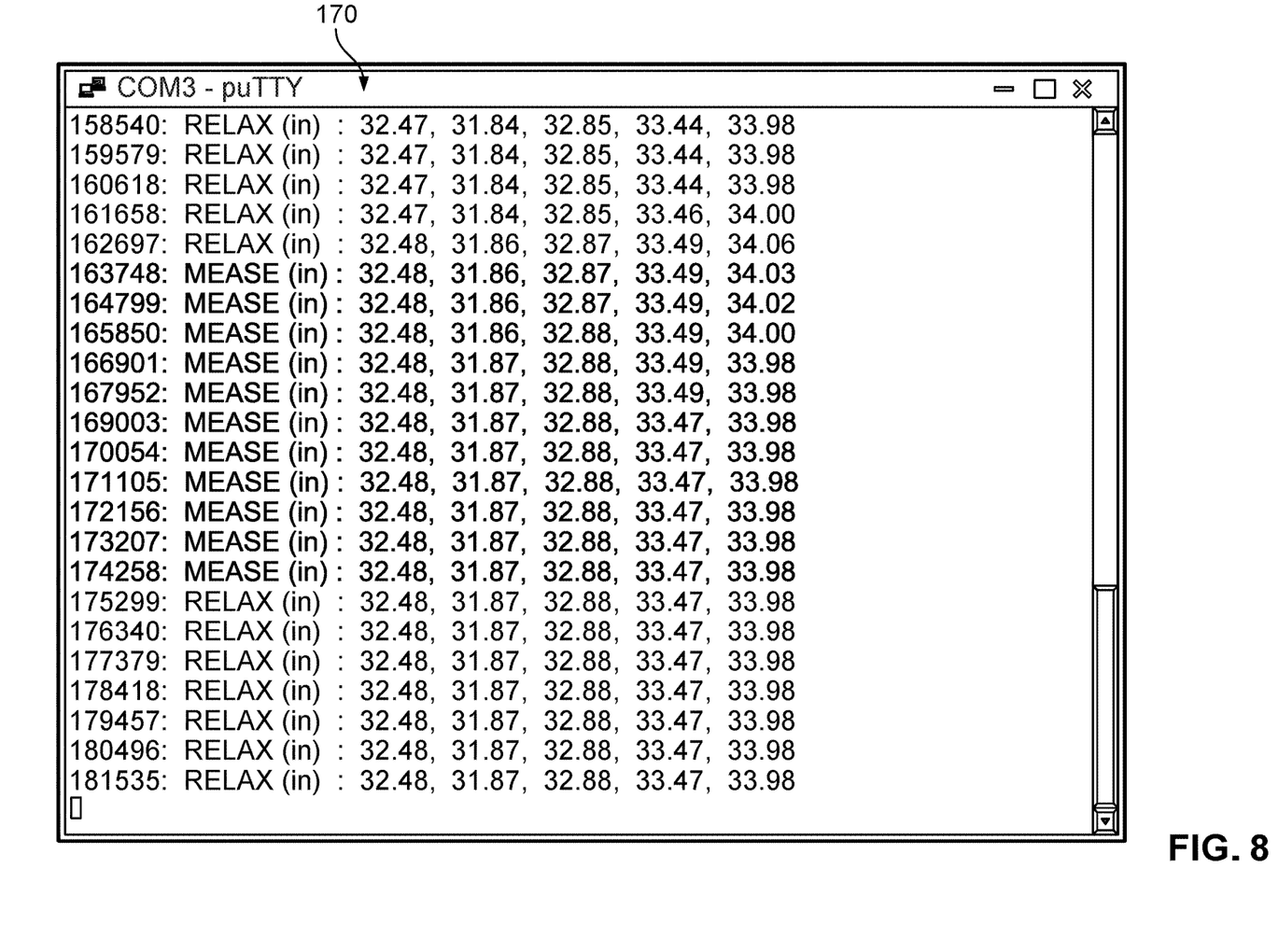
FIG. 8 is a screenshot of a viewing window displaying data output from the abdominal measurement apparatus of FIG. 1.

Referring to FIG. 8, an abdominal circumference, a type of the round, and an associated time stamp are outputted in a row to a viewing window 170 displayed on a monitor of the computer for each set of length measurements produced for each measurement device 122. Measuring the abdominal circumference at five locations allows determination of an optimal circumference that is associated with health risk for entry into an electronic medical record (EMR). In addition, an abdominal volume of the subject 101 can be calculated from this data. In some embodiments, the processing module 126 may be programmed to compute an abdominal volume of the subject 101 according to an algorithm. The outputted data can be stored in various types of files, such as a spreadsheet or a text file. In some implementations, the optimal circumference and/or computed abdominal volume can be stored in the EMR in association with a date, an identity of the subject 101, or other parameters.

In some implementations, the abdominal measurement apparatus 100 may be used to determine the abdominal circumference of a subject every 3 months to every 12 months, depending on a health state and a health objective of the subject. The abdominal measurement apparatus 100 provides an accurate, precise (e.g., repeatable) abdominal measurement that removes the variability associated with conventional manual measurement tapes used by subjects and clinicians to measure abdomens (e.g., waist circumference) of the subjects. Owing to the small footprint and light weight of the abdominal measurement apparatus 100, the abdominal measurement apparatus 100 may be transported easily and made readily available in a variety of settings, such as at a home, an office, a medical facility, or a fitness center.

Figure 9:
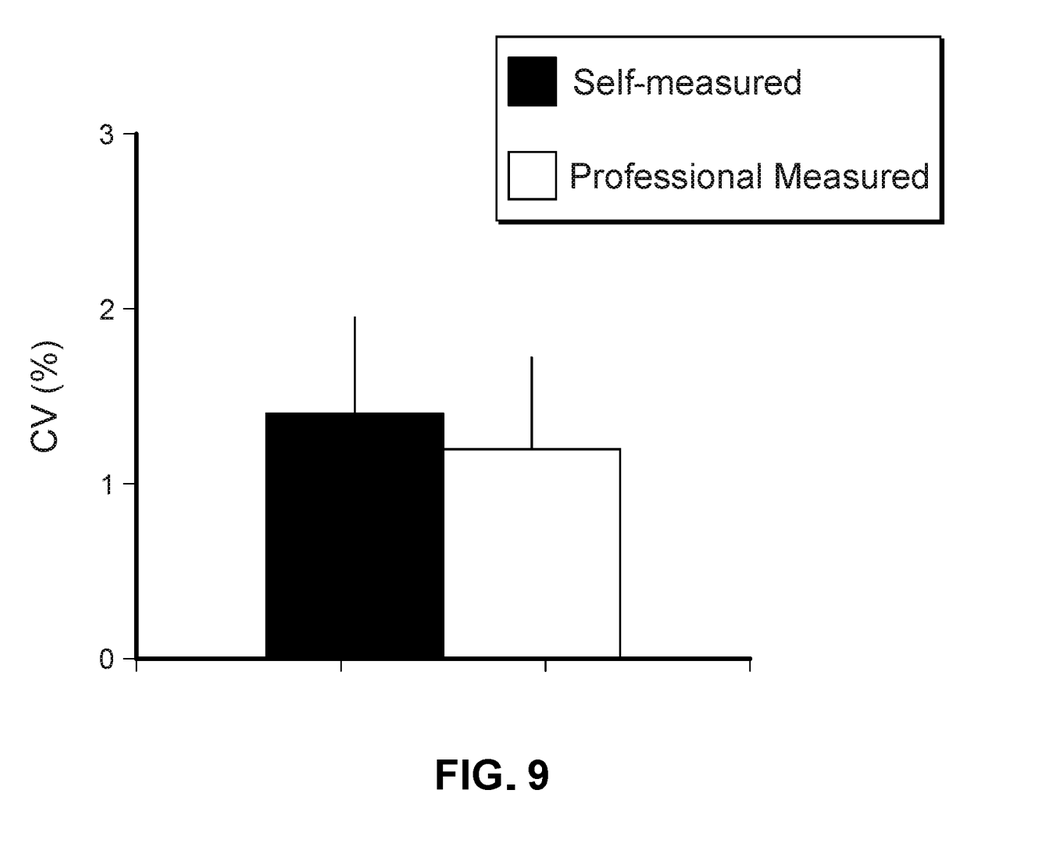
FIG. 9 is a graph of a coefficient of variation (CV) for replicate waist circumference measurements.

Testing of the abdominal measurement apparatus 100 has shown that, even an adult who is inexperienced in putting on and operating the abdominal measurement apparatus 100 can measure his or her waist circumference (e.g., for 5 days in a row) more reproducibly than can a highly trained operator using a standard measuring tape, as shown in FIG. 9.

A number of embodiments have been described. Nevertheless, it will be understood that various modifications may be made without departing from the spirit and scope of the present disclosure. For example, while the abdominal measurement apparatus 100 has been described as having certain dimensions, operational parameters, and material constituencies, in some embodiments, abdominal measurement apparatuses that are generally similar in construction and function to the abdominal measurement apparatus 100 may include different dimensions, operational parameters, and material constituencies.

While the abdominal measurement apparatus 100 has been described and illustrated as a wired apparatus, in some embodiments, an abdominal measurement apparatus that is similar in function and construction to the abdominal measurement apparatus 100 may include one or both of a wireless processing module and wireless user terminal and associated Bluetooth technologies.

While the abdominal measurement apparatus 100 has been described as being used to determine an optimally predictive abdominal circumference, in some embodiments, an abdominal measurement apparatus that is similar in function and construction to the abdominal measurement apparatus 100 may be designed to determine other indices or parameters associated with the abdomen, such as abdominal volume.

In certain embodiments, an abdominal measurement apparatus that is otherwise similar in function and construction to the abdominal measurement apparatus 100 may additionally include a distance sensor system for measuring anterior-posterior diameter, thereby improving volume measurements. For example, one or more distance sensors can be located at the front and/or back of the abdominal measurement apparatus to measure anterior-posterior distance. In one example, one distance sensor can be located at or close to the zipper 124 along a front portion of the abdominal measurement apparatus, and another distance sensor can be located at or close to the measurement device 122 along a rear portion of the abdominal measurement apparatus. In another example, two or more distance sensors can be mounted on different belts 134 close to the zipper 124 along a front portion of the abdominal measurement apparatus, and two or more distance sensors can be mounted on different belts 134 close to the measurement device 122 along a rear portion of the abdominal measurement apparatus.

Other embodiments are within the scope of the following claims.

What is claimed is:

1. An abdominal measurement apparatus, comprising:
a plurality of measurement devices, each measurement device comprising:
a first roller;
a second roller;
a first belt coupled to the first roller and configured to partially surround an abdomen; and
a second belt coupled to the second roller and configured to partially surround the abdomen,
wherein the first and second rollers rotate to automatically lengthen or shorten the first and second belts to maintain constant tensions in the first and second belts as the abdomen expands and contracts, and
wherein the measurement device is configured to determine a length of the first belt and a length of the second belt while the first belt and the second belt are maintained at the constant tensions;
wherein the plurality of measurement devices are configured to automatically maintain tensions of each first belt and each second belt of the plurality of measurement devices at the constant tensions.

2. The abdominal measurement apparatus of claim 1, further comprising a backpack to which the plurality of measurement devices are mounted, the backpack being adjustable to accommodate various sizes of subject torsos.

3. The abdominal measurement apparatus of claim 1, wherein each measurement device of the plurality of measurement devices is configured to acquire measurements at a predetermined frequency.

4. The abdominal measurement apparatus of claim 1, further comprising a processor in communication with the plurality of measurement devices.

5. The abdominal measurement apparatus of claim 4, wherein the processor is configured to receive measurements from the plurality of measurement devices and to output the measurements to a computing device.

6. The abdominal measurement apparatus of claim 5, wherein the processor is configured to wirelessly communicate with the computing device.

7. The abdominal measurement apparatus of claim 1, further comprising a user interface terminal by which the abdominal measurement apparatus can be controlled.

8. A method of measuring an abdomen, the method comprising:
receiving, by a processor, a plurality of signals that respectively indicate peripheral measurements of an abdomen, the plurality of signals generated by an abdominal measurement apparatus in contact with the abdomen, the abdominal measurement apparatus comprising:
a plurality of measurement devices, each measurement device comprising:
a first roller;
a second roller;
a first belt coupled to the first roller and configured to partially surround the abdomen; and
a second belt coupled to the second roller and configured to partially surround the abdomen,
wherein the first and second rollers rotate to automatically lengthen or shorten the first and second belts to maintain constant tensions in the first and second belts as the abdomen expands and contracts, and
wherein the measurement device is configured to determine a length of the first belt and a length of the second belt while the first belt and the second belt are maintained at the constant tensions;
wherein the plurality of measurement devices are configured to automatically maintain tensions of each first belt and each second belt of the plurality of measurement devices at the constant tensions; and
determining, by the processor, an index associated with the abdomen based on the plurality of signals indicating peripheral measurements of the abdomen.

9. The method of claim 8, further comprising adjusting a length of the first belt and the second belt by simultaneously rotating the first roller and second rollers in opposite roller directions.

10. The method of claim 8, wherein each first roller and second roller comprises a spring-loaded roller.

11. The method of claim 8, further comprising receiving, by the processor, the plurality of signals at a predetermined frequency.

12. The method of claim 8, wherein the index comprises an abdominal volume.

13. The method of claim 8, wherein the index comprises an abdominal circumference.

14. The abdominal measurement apparatus of claim 1, wherein the constant tensions are between about 4 pounds and about 7 pounds.

15. The method of claim 9, wherein the plurality of signals include counts per revolution of each roller.

* * * * *